United States Patent
Carter

[11] 3,988,385
[45] Oct. 26, 1976

[54] PROCESS FOR PRODUCING ETHYL FLUORIDE PRODUCT AND ALKYLATE PRODUCT IN HF ALKYLATION

[75] Inventor: Cecil O. Carter, Bartlesville, Okla.

[73] Assignee: Phillips Petroleum Company, Bartlesville, Okla.

[22] Filed: Oct. 15, 1975

[21] Appl. No.: 622,592

[52] U.S. Cl. .................... 260/683.42; 260/683.48
[51] Int. Cl.² ........................................... C07C 3/54
[58] Field of Search ............... 260/683.48, 683.49, 260/683.42

[56] References Cited
UNITED STATES PATENTS

| | | |
|---|---|---|
| 3,209,051 | 9/1965 | Bauer et al. .................... 260/683.48 |
| 3,253,054 | 5/1966 | Van Pool ....................... 260/683.48 |
| 3,751,517 | 8/1973 | Hutson, Jr. et al. ............ 260/683.48 |
| 3,763,265 | 10/1973 | Hutson, Jr. et al. ............ 260/683.48 |
| 3,919,342 | 11/1975 | Chapman ....................... 260/683.48 |

*Primary Examiner*—George Crasanakis

[57] ABSTRACT

The overhead stream of a deisobutanizer in an HF-alkylation plant is extracted with HF to produce a stream containing isobutane, HF and ethyl fluoride, which in turn is fractionated under a pressure of about 150 to 300 psig. The bottoms stream of this fractionation, then, is fractionated under a pressure of 50 to 145 psig to produce a relatively pure ethyl fluoride overhead stream and a relatively pure HF bottoms stream.

6 Claims, 1 Drawing Figure

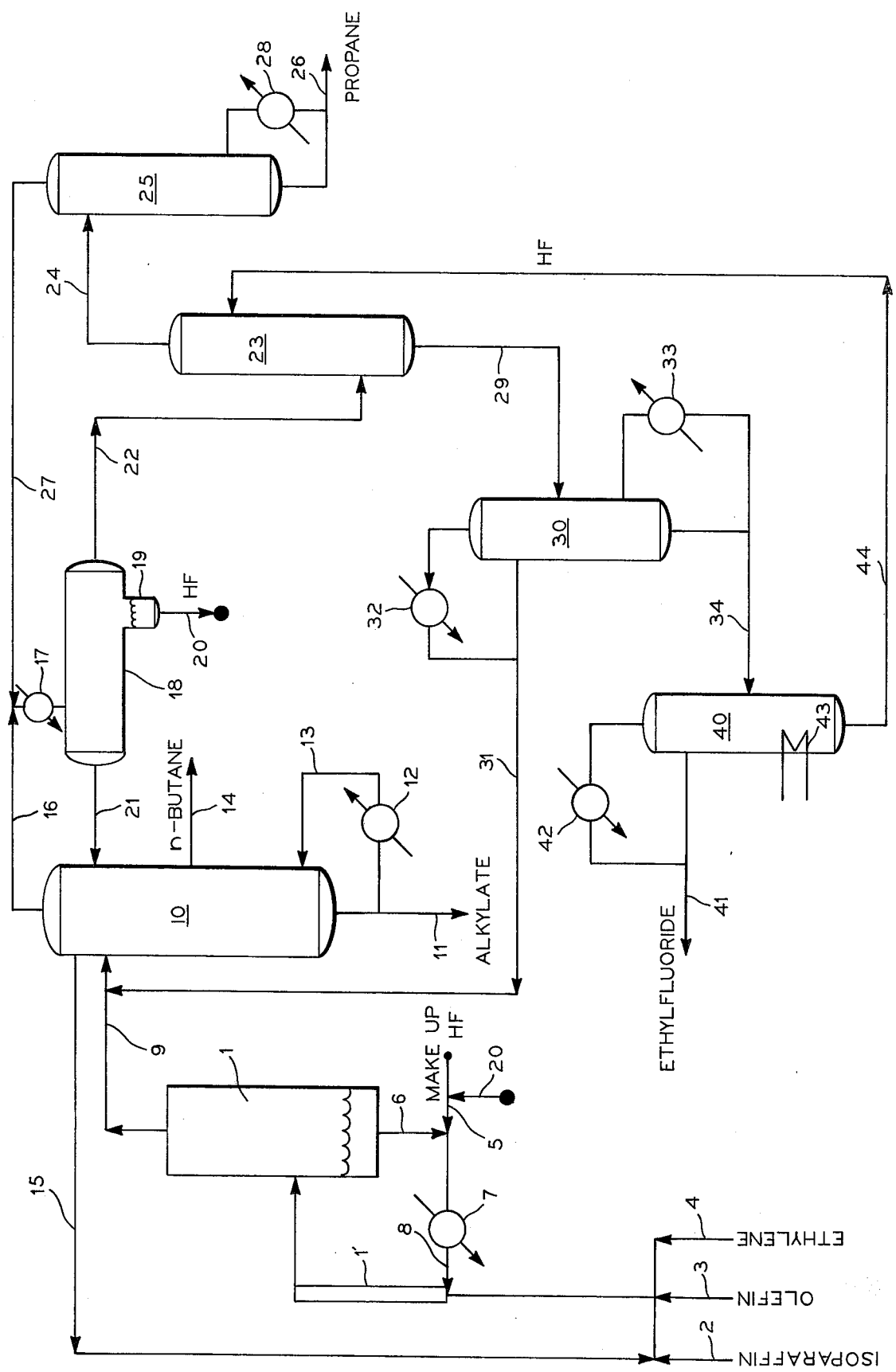

PROCESS FOR PRODUCING ETHYL FLUORIDE PRODUCT AND ALKYLATE PRODUCT IN HF ALKYLATION

This invention pertains to the separation of a mixture of hydrogen fluoride, ethyl fluoride and an isoparaffin. In one of its more specific aspects, this invention pertains to an alkylation process in which ethyl fluoride also is produced.

BACKGROUND OF THE INVENTION

It is known in the art that an alkylate can be produced from olefins and isoparaffins using HF as an alkylation catalyst. The octane number of this alkylate can be further improved by carrying out the alkylation process in the presence of ethyl fluoride as a promoter. Ethyl fluoride is either produced in the alkylation reactor by introducing ethylene into the reactor containing HF or it is added separately to the alkylation reactor. Since the HF catalyst and the ethyl fluoride are expensive compounds, it would be desirable to have a process available which readily recovers ethyl fluoride from the system so that it can be used as the promoter, e.g. in cases where no ethylene is available or in cases where it is desirable to add ethyl fluoride to compensate for losses of ethyl fluoride in the process of producing alkylates.

THE INVENTION

It is thus one object of this invention to provide a process for the production of ethyl fluoride.

Another object of this invention is to provide a process for separating ethyl fluoride from a stream comprising an isoparaffin, HF and ethyl fluoride.

A further object of this invention consists in the provision of a process for the production of an alkylate and ethyl fluoride.

Still a further object of this invention is to provide a process for the production of an alkylate and ethyl fluoride in relatively pure form.

In accordance with this invention, I have now found that HF and ethyl fluoride can be recovered from a mixture of HF, ethyl fluoride and an isoparaffin by fractionally distilling the mixture of HF, ethyl fluoride and isoparaffin in a first column under a pressure in the range of about 150 to 300 psig, and by fractionally distilling the liquid bottoms stream from said first column in a second zone under a pressure in the range of about 50 to 145 psig to form an overhead stream consisting essentially of ethyl fluoride and a bottoms stream consisting essentially of HF. The relatively pure ethyl fluoride overhead stream of the second column can be used for various purposes. Particularly, this ethyl fluoride material can be used as the promoter in an HF alkylation process.

More specifically and in accordance with a presently preferred embodiment of this invention, the first column is operated under a pressure of 150 to 290 psig and a temperature of 160° to 215° F at the top of the column and at a pressure of 152 to 300 psig and a temperature of 210° to 260° F at the bottom; pressures of 200 to 250 psig are preferred for the first column. Correspondingly, the second column is operated under a pressure of 50 to 140 psig and a temperature of 30° to 90° F at the top and under a pressure of 55 to 145 psig and a temperature of 160° to 190° F at the bottom; for this second column pressures of 25 to 125 psig are presently most preferred.

In accordance with one embodiment of this invention, and in order to minimize the losses of ethyl fluoride by polymerization, it is presently preferred to operate the first column with a kettle temperature of about 230° to about 250° F and to operate the second column with a kettle temperature of about 150° to about 175° F. Most preferably, the kettle temperature of the first column is about 240° F and the kettle temperature of the second column is about 160° F.

Another embodiment of this invention resides in an overall process for the production of an alkylate and ethyl fluoride. In accordance with this embodiment of this invention, an isoparaffin and an olefin are reacted in the presence of HF and ethyl fluoride in an alkylation reaction zone to form an alkylate, the alkylate is removed from the reactor effluent, and a stream consisting essentially of HF, ethyl fluoride and isoparaffin is removed from the reaction zone. The HF alkylation in the presence of ethyl fluoride is known from U.S. Pat. No. 3,842,140. From the stream consisting essentially of HF, ethyl fluoride and isoparaffin, a relatively pure stream of HF and a stream of relatively pure ethyl fluoride are removed as has been described above.

The reactor effluent coming from the alkylation reactor, preferably after removal of the alkylate, and in accordance with a further embodiment of this invention, is passed through an extractor to recover propane from this material, and the liquid bottoms stream from the second column consisting essentially of HF is introduced into said extractor as the extractant to remove ethyl fluoride from propane. A mixture of propane and HF leaves this extractor overhead and the propane is removed from this mixture in an HF stripping column. Propane is withdrawn from this stripping column at the bottom, whereas HF leaves the stripping column overhead.

In accordance with still a further embodiment of this invention, the alkylation reactor effluent, after removal of the alkylate, is introduced into a settler for phase separation. HF accumulating in the lower section of this settler is preferably reintroduced into the alkylation reaction section.

A further embodiment of this invention provides for the production of ethyl fluoride from ethylene and HF. In accordance with this embodiment, a stream of ethylene and a stream of HF are introduced into the alkylation reaction section, in which ethyl fluoride is formed from these constituents. This part of the overall process is known in the art. The ethyl fluoride is thereafter recovered in pure form as has been described above. This embodiment of the invention combines the HF alkylation and the separation of ethyl fluoride and HF.

In accordance with another embodiment of this invention, the overhead stream from the first column operated under the high pressure, which consists essentially of isoparaffin, is reintroduced into a main column in which the effluent from the alkylation reactor is fractionated to result in a bottoms stream of alkylate.

The invention will be still more fully understood from the following description of the drawing.

Into an alkylation riser reaction 1' there are introduced a stream of isoparaffin, such as isobutane via line 2, a stream of olefin (e.g. propylene and/or butylenes) via line 3, a stream of ethylene via line 4, and a stream of HF via line 5. The reaction product flows into a settler 1. From the settler 1 of the alkylation, a stream of HF catalyst is withdrawn via line 6. This stream of catalyst is cooled in cooler 7 and reintroduced into the riser reactor 1' via line 8.

The reaction effluent is withdrawn from the alkylation reactor-settler 1 via line 9. This stream of reactor effluent is introduced into a main column 10. From this column 10 which contains, e.g. 100 trays, a bottoms stream of alkylate is withdrawn via line 11. A portion of the alkylate withdrawn from the bottom is heated in a reboiler 12, and the heated and partially vaporized alkylate is reintroduced into the main column 10 via line 13. A side stream of n-butane vapor is withdrawn from the main column 10 via line 14.

Isobutane liquid is withdrawn from the column 10 via line 15. This stream of isobutane is reintroduced into the alkylation reactor-settler 1, together with the make-up or charge isobutane via line 2.

An overhead stream of vapor consisting essentially of propane, isobutane, HF, and ethyl fluoride is withdrawn via line 16 from the main column 10. This stream is cooled and condensed in exchanger 17 and introduced into the settler 18. From the settling leg 19 of the settler 18, HF is withdrawn via line 20. The HF withdrawn is reintroduced into the alkylation reaction zone-settler 1, as indicated by the two black dots in the drawing. A portion of the lighter liquid or hydrocarbon phase in the settler 18 is reintroduced as a reflux stream via line 21 into the main column 10. Another stream of the lighter phase in the settler 18 consisting essentially of HF, ethyl fluoride, propane and isobutane, is passed via line 22 to an extracting unit 23. This stream is extracted with HF in the extractor 23, which HF is introduced via line 44, and which serves to extract ethyl fluoride from the hydrocarbon feed stream 22. An overhead stream consisting essentially of propane and HF is withdrawn from said extractor 23 via line 24.

The stream of propane and HF is introduced via line 24 into HF stripper unit 25. From this HF stripper unit 25, a bottoms stream of propane is withdrawn via line 26, whereas an overhead stream consisting essentially of HF and some propane is withdrawn via line 27 and passed through cooler 17 into settler 18.

The HF stripper 25 is provided with a reboiler 28, in which part of the bottoms stream is reboiled, in order to provide the heat necessary for the fractionation in the HF stripper 25.

A bottoms stream consisting essentially of HF, ethyl fluoride and isobutane is withdrawn via line 29 from the extractor 23. This bottoms stream is introduced into a first distillation column 30, which is operated at a pressure in the range of 200 to 250 psig. Isobutane vapors from the first distillation column 30 are condensed in condenser 32, a portion of which is reintroduced as reflux into column 30 and the balance withdrawn via line 31.

From the bottom of the first distillation column 30, a stream consisting essentially of HF and ethyl fluoride is withdrawn. Part of this bottoms stream is heated in a reboiler 33 in order to provide the necessary heat for the distillation column 30, whereas the other portion of the bottoms stream is passed via line 34 into a second distillation column 40. An overhead stream consisting of essentially pure ethyl fluoride vapors are condensed in condenser 42, a portion of which is reintroduced as reflux into column 40 and the balance withdrawn via line 41. The heat necessary for the operation of the second distillation column 40 is provided by a heater 43 in the bottom of the second distillation column 40.

From the bottom of the second distillation column 40, a stream of essentially pure HF is withdrawn via line 44. This HF stream is introduced as the extractant into the extractor 23.

The invention will be still more fully understood from the following examples showing preferred embodiments of this invention; these examples are not intended to limit the invention unduly.

EXAMPLE I

Two-Step Recovery of Pure Ethyl Fluoride

Into the lower third of a distillation unit having a packed column of 72 inches length and 2 inches diameter, 14.3 pounds/hour of feed having the composition shown in the following table were continuously introduced. The kettle was heated to a temperature of 242° F, and the column was operated under a pressure of 234 psig. The overhead product was condensed and collected. The condensed overhead product (0.42 pounds/hour) and the kettle product (13.88 pounds/hour) were analyzed and the compositions shown in the following Table I were found:

Table I

First Column (30)

| Composition | Feed (29) Wt. % | Overhead Product (31) Wt. % | Kettle Product (34) Wt. % |
|---|---|---|---|
| $H_2O$ | 0.50 | — | 1.00 |
| HF | 86.00 | 10.7 | 88.30 |
| Acid-soluble oils | 2.20 | — | 2.40 |
| Propane | 0.26 | 3.2 | — |
| Isobutane | 5.59 | 68.4 | 0.24 |
| Ethyl fluoride | 4.51 | 7.2 | 7.86 |
| n-Butane | 0.41 | 3.9 | 0.20 |
| Isopentane and heavier hydrocarbons | 0.53 | 6.6 | — |
| Total | 100.00 | 100.0 | 100.00 |

The kettle product obtained was then continuously introduced (13.88 pounds/hour) into the kettle of a second distillation unit equipped with a packed column of 72 inches length and 2 inches internal diameter. The column was operated at 100 psig and the kettle was heated to a temperature of 160° F. The overhead product (1.32 pounds/hour) of this distillation unit was also condensed and the recovered overhead liquid, as well as the kettle product (12.56 pounds/hour) were analyzed. The overhead and kettle product quantities are based on HF balance. The results are shown in the following Table II.

Table II

Second Column (40)

| Composition | Feed (34) Wt. % | Overhead Product (41) Wt. % | Kettle Product (44) Wt. % |
|---|---|---|---|
| $H_2O$ | 1.0 | — | 1.09 |
| HF | 88.3 | 14.5 | 96.29 |
| Acid-soluble oils | 2.4 | 0 | 2.61 |
| Propane | — | — | — |
| Isobutane | 0.24 | 2.5 | — |
| Ethyl fluoride | 7.86 | 80.9 | — |
| n-Butane | 0.20 | 2.1 | — |

From the results shown in the above tables, it can be seen that by this two-stage distillation under the specific pressures given, an essentially pure stream 41 of ethyl fluoride (after HF removal, e.g. by water wash) and an essentially pure stream of hydrogen fluoride 44 can be produced. The overhead stream 31 of the first column consists essentially of isobutane and can be advantageously reintroduced into the main column of the alkylation plant.

Example II

Typical Operation in an Alkylation Plant

This calculated example is based on the results obtained above. The example shows in the following table the conditions, compositions, and flow rates of the various streams and units. The reference numerals refer to the drawing.

The compositions and flow rates are based on a HF-alkylation reaction in which propylene and butylenes are fed as the olefin charge and isobutane is fed as the isoparaffin charge to an alkylation unit. In addition, HF catalyst and ethylene are fed to the alkylation unit. The isobutane to olefin mole ratio is 10.8 to 1 (volume ratio 13.6 to 1). The HF catalyst to hydrocarbon volume ratio is 4 to 1; the alkylation temperature is 90° F and the pressure sufficient to maintain the liquid phase in the alkylation unit. The product obtained is passed to fractionation. Alkylate is removed as a bottom stream, n-butane vapor is removed as a side stream below the fractionation tower feed inlet and liquid isobutane is removed from the fractionation tower above the fractionation tower feed inlet and is recycled. A vapor stream 22 is removed overhead from the fractionation tower, condensed and further processed as described above in accordance with the present invention. The stream compositions and flow quantities are shown in the following Table III.

TABLE III

| | Amounts |
|---|---|
| Hydrocarbon (22), B/H | 341 |
| Composition, wt. % | |
| H$_2$O | 0.5 |
| HF | 13.8 |
| Propane | 7.2 |
| Isobutane | 31.9 |
| Normal Butane | 0.1 |
| Isopentane and heavier | — |
| Acid Soluble Oils | 0.3 |
| Ethyl Fluoride | 46.2 |
| HF (44), B/H | 1255 |
| 96.3 wt. % HF | |
| Extract Yield (29), B/H | 1596 |
| Composition, wt. % | |
| H$_2$O | 1.1 |
| HF | 84.1 |
| Propane | 0.4 |
| Isobutane | 4.8 |
| Normal Butane | 0.02 |
| Isopentane and heavier | — |
| Acid Soluble Oils | 1.5 |
| Ethyl Fluoride | 8.1 |
| Total | 100.02 |
| Conditions in Extractor: | |
| Pressure, psig | To maintain liquid phase |
| Temperature, ° F | 90 |
| Product (31), B/H | 147 |
| Composition, wt. % | |
| H$_2$O | — |
| HF | 11.5 |
| Propane | 3.4 |
| Isobutane | 73.2 |
| Normal Butane | 4.2 |
| Isopentane and heavier | — |
| Acid Soluble Oils | — |
| Ethyl Fluoride | 7.7 |
| Total | 100.0 |
| Bottoms (34), B/H | 1449 |
| Composition, wt. % | |
| H$_2$O | 1.2 |
| HF | 88.7 |
| Propane | 0.2 |
| Isobutane | 0.2 |
| Normal Butane | 0.0 |
| Isopentane and heavier | — |
| Acid Soluble Oils | 1.6 |
| Ethyl Fluoride | 8.1 |
| Overhead (41), B/H | 193 |
| Composition, wt. % | |
| H$_2$O | — |
| HF | 14.5 |
| Propane | 2.4 |
| Isobutane | 2.6 |
| Normal Butane | 0.2 |
| Isopentane and heavier | — |
| Acid Soluble Oils | — |
| Ethyl Fluoride | 80.4 |
| Tower 30: | |
| Pressure, psig | |
| Top | 234 |
| Bottom | 236 |
| Temperature, ° F | |
| Top | 192 |
| Bottom | 242 |
| Tower 40: | |
| Pressure, psig | |
| Top | 100 |
| Bottom | 105 |
| Temperature, ° F | |
| Top | 67 |
| Bottom | 190 |

Tower 30, for this size operation, is 8 feet in diameter and has 50 trays. Tower 40, similarly, has 7 feet diameter and 30 trays.

Reasonable variations and modifications, which will be apparent to those skilled in the art, can be made in this invention without departing from the spirit and scope thereof.

I claim:
1. A process for producing ethyl fluoride product and an alkylate product comprising
   a. introducing a stream of isoparaffin selected from the group consisting of isobutane, isopentane and mixtures thereof, a stream of an olefin selected from the group consisting of propylene, butylenes, and mixtures thereof, and a stream of ethylene into an alkylation reaction zone,
   b. reacting said paraffin and said olefin in said alkylation reaction zone in the presence of a catalyst comprising HF to form a reaction product stream comprising an alkylate, isoparaffin, HF, ethyl fluoride and propane,
   c. passing said reaction product stream into a separation zone,
   d. removing a stream of said alkylate product from said reaction product stream in said separation zone,
   e. removing a stream of isoparaffin from said reaction product stream in said separation zone,
   f. removing a stream consisting essentially of HF, ethyl fluoride, propane and isoparaffin from said separation zone,
   g. extracting ethyl fluoride from said stream of step (f) with liquid HF and passing said extracted stream consisting essentially of HF, ethyl fluoride and isoparaffin into a first column,
   h. fractionally distilling said extracted stream consisting essentially of HF, ethyl fluoride and isoparaffin in said first column under a pressure in the range of about 150 to 300 psig to form an overhead stream consisting essentially of said isoparaffin and a bottoms stream consisting essentially of HF and ethyl fluoride,
   i. passing said bottoms stream consisting essentially of HF and ethyl fluoride into a second column,
   j. fractionally distilling said bottoms stream consisting essentially of HF and ethyl fluoride in said sec- ond column under a pressure in the range of about 50 to 145 psig to form an overhead stream consisting essentially of ethyl fluoride and a bottoms stream consisting essentially of HF, and k. recovering said overhead stream as said ethyl fluoride product of the process.

2. A process according to claim 1 wherein said separation zone comprises a main column, a settler and an extractor, said process comprising the steps of
a. passing said reaction product stream into said main column,
b. withdrawing said stream of alkylate product from said main column as a liquid bottoms stream,
c. withdrawing a stream comprising HF, ethyl fluoride, isopuroffin and propane from said main column as an overhead stream,
d. introducing said stream comprising HF, ethyl fluoride isoparaffin and propane into said settler,
e. withdrawing an HF liquid stream from said settler,
f. withdrawing a stream comprising HF, ethyl fluoride, isoparaffin and propane from said settler,
g. introducing said stream comprising HF, ethyl fluoride, paraffin and propane withdrawn from said settler into said extractor,
h. introducing a stream of HF as the extractant into said extractor,
i. withdrawing a bottoms stream from said extractor, which bottoms stream comprises HF, ethyl fluoride, isoparaffin and essentially no propane,
j. withdrawing a stream overhead from said extractor, which stream comprises HF and propane, and
k. introducing said bottoms stream withdrawn from said extractor into said first column.

3. A process in accordance with claim 2 wherein said bottoms stream from said second column consisting essentially of HF is introduced into said extractor as said HF stream.

4. A process in accordance with claim 2 wherein said stream of HF withdrawn from said settler is reintroduced into said alkylation reaction zone.

5. A process in accordance with claim 2 wherein said overhead stream from said first column consisting essentially of isoparaffin is reintroduced into said main column.

6. A process in accordance with claim 2 wherein said overhead stream from said extractor is introduced into a depropanizing column, wherein a stream of propane is withdrawn from the bottom of said depropanizing column, wherein a stream of HF and propane is withdrawn overhead from said depropanizing column and wherein said stream of HF and propane is introduced into said settler.

* * * * *